United States Patent
Bockenheimer et al.

(10) Patent No.: US 7,503,224 B2
(45) Date of Patent: Mar. 17, 2009

(54) VACUUM SENSOR APPLICATION AND METHOD FOR NONDETACHABLY JOINING A SENSOR WORKPIECE TO A BODY COMPONENT

(75) Inventors: Clemens Bockenheimer, Schiffweiler (DE); Heiner Stehmeier, Bremen (DE)

(73) Assignee: Airbus Deutschland GmbH, Hamburg (DE)

( * ) Notice: Subject to any disclaimer, the term of this patent is extended or adjusted under 35 U.S.C. 154(b) by 433 days.

(21) Appl. No.: 10/596,203

(22) PCT Filed: Dec. 10, 2004

(86) PCT No.: PCT/EP2004/014106

§ 371 (c)(1),
(2), (4) Date: Jun. 2, 2006

(87) PCT Pub. No.: WO2005/059522

PCT Pub. Date: Jun. 30, 2005

(65) Prior Publication Data

US 2008/0264177 A1    Oct. 30, 2008

(30) Foreign Application Priority Data

Dec. 12, 2003  (DE) .............................. 103 58 772
Nov. 26, 2004  (DE) ....................... 10 2004 057 290

(51) Int. Cl.
G01N 19/08    (2006.01)
(52) U.S. Cl. ........................................................ 73/799
(58) Field of Classification Search .................. 73/799
See application file for complete search history.

(56) References Cited

U.S. PATENT DOCUMENTS 5,571,410 A    11/1996    Swedberg et al.

(Continued)

FOREIGN PATENT DOCUMENTS

DE         10056908 A1       5/2002

(Continued)

OTHER PUBLICATIONS

Speckmann, H et al: Structural Health Monitoring(SHM)—"Overview on Technologies Under Development" retrieved from the internet on Apr. 20, 2005.

(Continued)

*Primary Examiner*—Andre J Allen
(74) *Attorney, Agent, or Firm*—Christopher Paradies; Fowler White Boggs P.A.

(57) ABSTRACT

Vacuum sensor application and method for firmly joining a sensor workpiece to a body component, where a) firstly, an adhesive layer which is provided by a cross-linked transfer contact adhesive is laminated to a sensor contact surface of the sensor workpiece, b) then, by using known radiation methods, the geometric patterns of a plurality of galleries to be arranged in a laminar fashion are transferred to the sensor contact surface by a light beam that penetrates the transfer contact adhesive, are subsequently introduced into the sensor workpiece and, in the process, are removed congruently with the structures of the adhesive layer introduced into the sensor workpiece, c) the adhesive-laminated patterned sensor contact surface is then arranged on a defined surface region of the body component surface, d) after that, a mechanical pressure is exerted on the two joint partners, with which the adhesive-laminated patterned sensor contact surface and the body component surface region (3) are pressed together.

48 Claims, 3 Drawing Sheets

U.S. PATENT DOCUMENTS 6,539,776 B2 * 4/2003 Davey .......................... 73/37
2002/0002866 A1 1/2002 Davey

FOREIGN PATENT DOCUMENTS

DE 10056908 A1 5/2002
DE 10105893 A1 8/2002

OTHER PUBLICATIONS

The International Search Report from the European Patent Office for PCT/EP2004/014106 dated Apr. 20, 2005.

Speckmann, H. et al, Structural Health Monitoring (SHM)—Overview On Technologies Under Development, http://www.ndt.net/article/wendt2004/pdf/aerospace/563_henrich.pdf, 4 pages.

* cited by examiner

VACUUM SENSOR APPLICATION AND METHOD FOR NONDETACHABLY JOINING A SENSOR WORKPIECE TO A BODY COMPONENT

FIELD OF THE INVENTION

The present invention relates to the field of Structural Health Monitoring (SHM) or vacuum sensors. In particular, the present invention relates to a method of firmly joining a sensor workpiece to a body component, and to a vacuum sensor.

TECHNOLOGICAL BACKGROUND

DE 100 56 908 A1 and U.S. Pat. No. 5,571,410 A both describe processes which use laser radiation to produce channel-like structures in components and then close these by laminating or welding a film on.

These two processes respectively propose solutions for producing channel-like structures whose fault-free and reproducible use for the implementation of "Structural Health Monitoring" on structures will not be beyond all doubt. In addition, viewed from technological aspects, no efficient implementation of a vacuum sensor application is assumed.

SUMMARY OF THE INVENTION

Accordingly, there may be a need for specifying improved solutions for a vacuum sensor application and a method for non-detachably joining a vacuum sensor to a body component surface, it being e.g. possible for crack finding in joints on a structure to be monitored continuously with the application.

Such vacuum sensor application may be implemented with the method according to an exemplary embodiment of the present invention in an efficient manner and without additional effort on reworking, the intention being to achieve fault-free and reproducible use for the implementation of "Structural Health Monitoring" on structures.

It is believed that by the features as specified in claims 1, 15, 47 and 48, an improved sensor or method may be provided, which is believed to meet the above need. Expedient refinements and development of these measures are specified in the further claims.

The invention relates to a vacuum sensor application for the implementation of "Structural Health Monitoring" (SHM) and a method for nondetachably joining a sensor workpiece to a body component. A vacuum sensor application and a method for its implementation are specified with which a secure and reproducible application of vacuum sensor technology using vacuum sensors for crack detection during mechanical tests on "coupon", "component" and "full scale" test items under test and also "Structural Health Monitoring" (SHM) on structures are implemented, in order to monitor the action of finding cracks in joints, for example in aircraft operation. This vacuum sensor application will be able to be implemented in an efficient manner without additional effort on reworking in any process, the application guaranteeing fault-free and reproducible use, which is assisted by vastly improved adhesive properties of the structure-monitoring vacuum sensors.

DETAILED DESCRIPTION OF EXEMPLARY EMBODIMENTS

The invention will be described in more detail with reference to exemplary embodiments using the appended drawings, in which.

Figure 1:
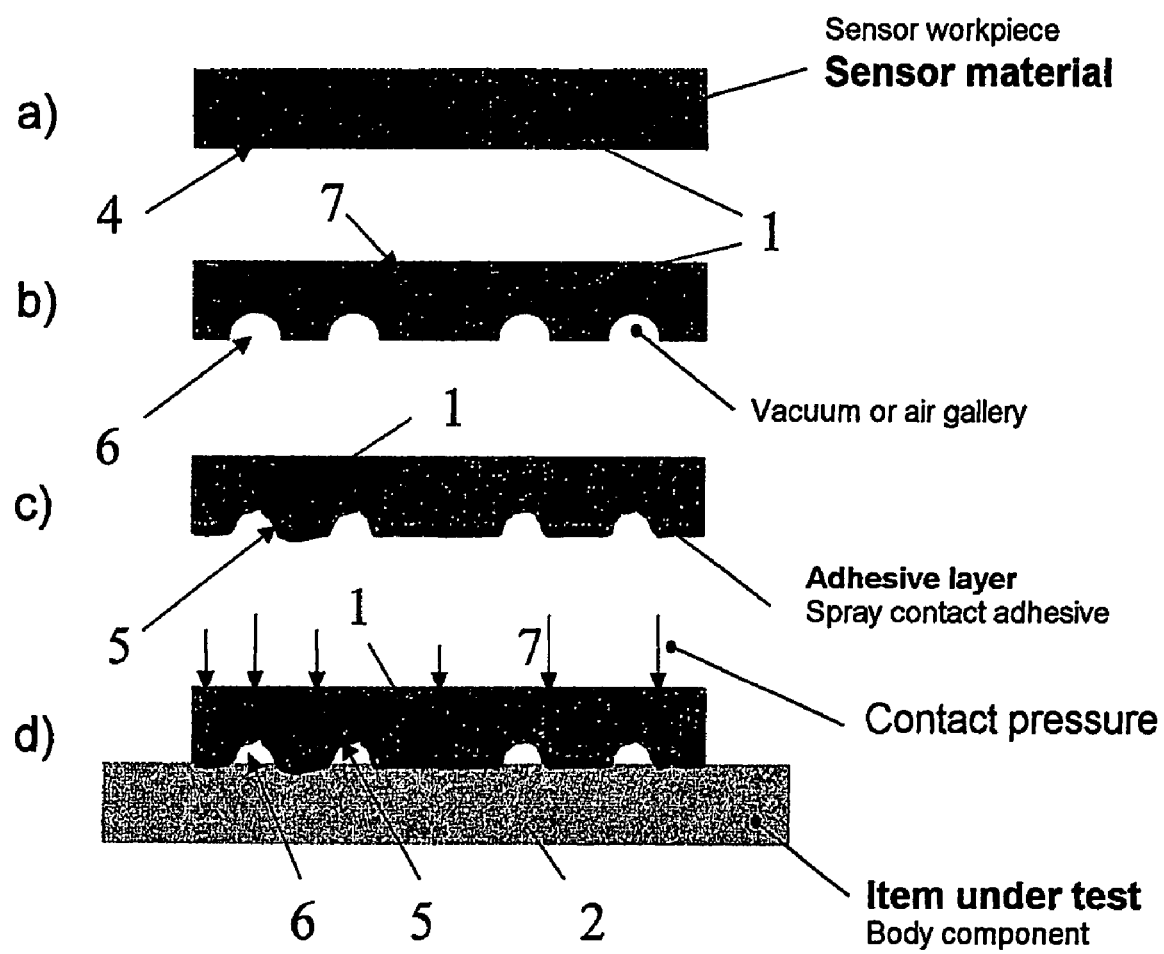
FIG. 1 shows a sectional view of a vacuum sensor arrangement.

The application of vacuum sensors for finding cracks in the joints on structures (structural surfaces) may be implemented in the following way as shown in FIG. 1. Firstly, the vacuum and air galleries are introduced into the sensor workpiece (sensor material), that is to say into the surface of the sensor, with the aid of laser lithography, following the pattern of FIGS. 1a, 1b. After that, the application of the non-crosslinked adhesive is applied to the lithographed surface in a spray process following the pattern of FIG. 1c. In this way, the galleries (vacuum and air galleries) are filled with adhesive to a good extent. As a result of the adhesive application in the spray process, only the use of a non-crosslinked adhesive is possible. In addition, the application of adhesive by lithography limits the maximum layer thickness of adhesive, since otherwise the vacuum and air galleries would be blocked. The adhesive bonding of the sensor to the surface of the item under test is illustrated in FIG. 1d, although this can be carried out only under an undefined and non-reproducible contact pressure.

In the application phase, the vacuum sensors are loaded dynamically-mechanically in a complex way in the joints. Here, leakage and blocking of the vacuum and air galleries frequently occurs in the bonded connections between sensor and surface of the item under test. The occurrence of leaks can be traced back to a) the excessively low layer thickness of the contact adhesive, which reduces the dynamic adhesion of the contact adhesive to the surface of the joint parts under the loading which occurs, b) to the increased tendency of the non-crosslinked spray adhesive to creep, c) to the undefined and non-reproducible contact pressure, which causes excessively weak and undefined adhesion of the contact adhesive to the surface of the joint parts. The blockages are triggered by a) the non-crosslinked contact adhesive flowing into the vacuum and air galleries and b) by the adhesive already present in the vacuum and air galleries under the action of the riveting forces or an excessively high contact pressure during the adhesive bonding of the sensors.

Figure 2:
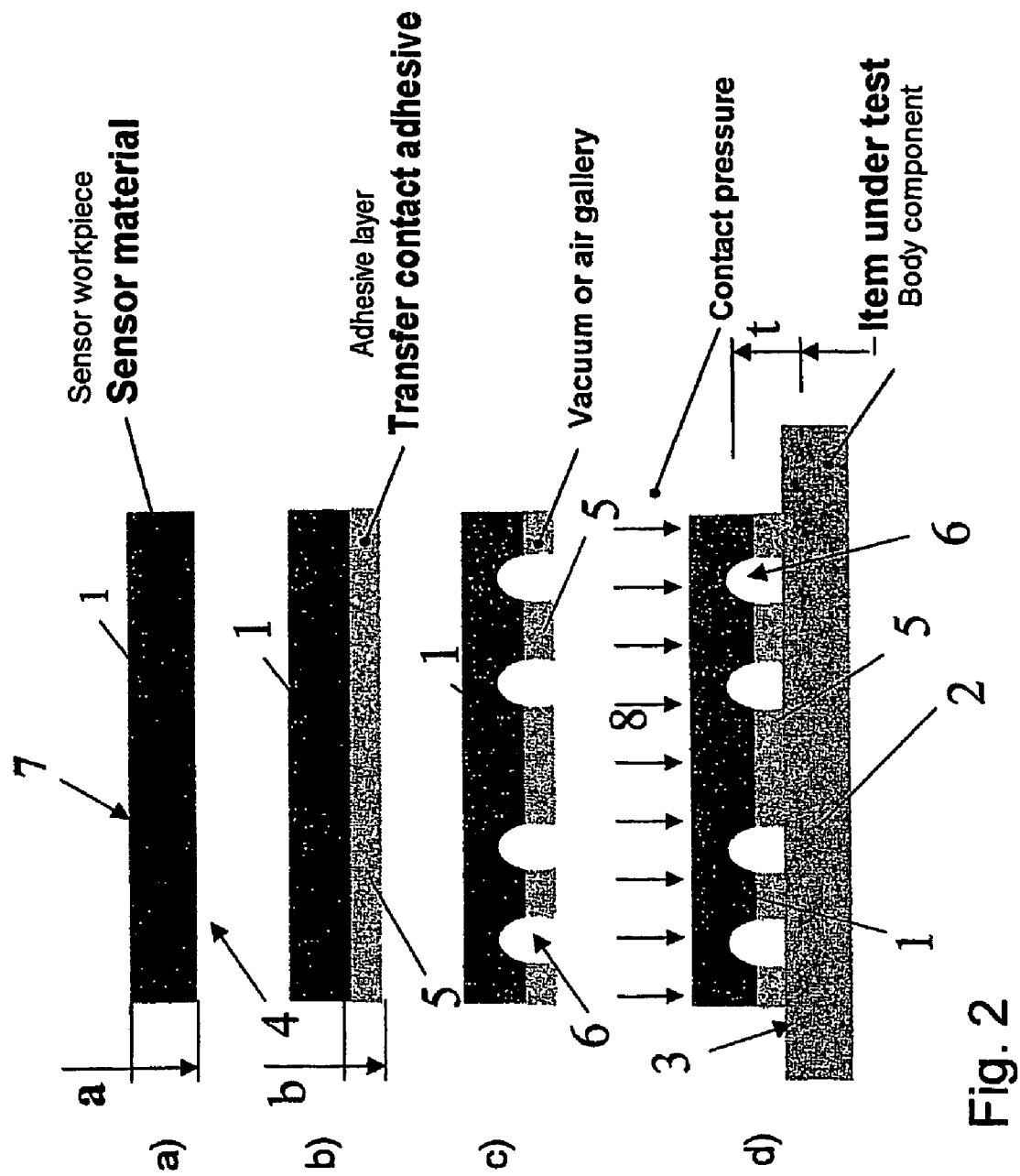
FIG. 2a shows a longitudinal section of an individual sensor workpiece according to an exemplary embodiment of the present invention (unrolled sensor material, extended embodiment)
FIG. 2b shows the sensor workpiece according to FIG. 1 with a contact adhesive laminated onto the sensor contact surface according to an exemplary embodiment of the present invention.
FIG. 2c shows the adhesive-laminated sensor workpiece according to FIG. 2b with the removed galleries according to an exemplary embodiment of the present invention.
FIG. 2d shows the adhesive-laminated sensor workpiece positioned on a body component with the architecture of removed galleries according to FIG. 2c according to an exemplary embodiment of the present invention.

The following explanations relate initially to the presentation of a method for non-detachably joining a sensor workpiece 1 to a body component 2, in which the sensor workpiece 1 is positioned on a body component surface region 3. This sensor workpiece 1 is intended to be joined nondetachably to the body component 2 within a defined region of the body component surface. This sensor workpiece 1, which is shown in FIG. 2a, is composed of a sensor material which is suitable for the implementation of the sensor function of a vacuum sensor.

The method proposed comprises the following steps, specified generally. Accordingly, first of all a) it is proposed that, onto what is known as a sensor contact surface 4 of the sensor workpiece 1, an adhesive layer 5 is laminated which, with a view of FIG. 2b, rests evenly on the surface. This adhesive layer 5 is composed of an (already) crosslinked transfer contact adhesive, which is implemented with a defined layer thickness. The transfer contact adhesive itself can be obtained from the provider with a variable layer thickness, which is supplied on what is known as a transfer roll. According to a further step b), the patterns of a plurality of galleries 6, what are known as vacuum and/or air galleries, are transferred to an adhesive-laminated sensor contact surface 4 [onto the adhesive-laminated surface region of a contact surface] of the sensor workpiece 1, following the pattern of FIG. 2c, by applying known radiation methods, for example with the aid of laser lithography, directly by using a light beam, for example a laser beam, which passes through the adhesive layer 5 [that is to say penetrating through the transfer contact adhesive], and is (subsequently) introduced into the sensor workpiece 1. In the process, the geometric patterns of those galleries 6 are removed so as to coincide with the structures of the adhesive layer 5 introduced into the sensor workpiece 1. These so-called galleries 6, which are machined into the aforementioned sensor contact surface 4 lying parallel beside one another, generally have a uniform gallery cross section of, for example, a parabolic form, the opening of the parabola terminating the sensor contact surface 4.

It would also be conceivable, however, for those galleries 6 to be machined into the sensor workpiece 1 with a different geometric configuration and different gallery cross section. There is also the possibility that the patterns of the galleries 6 are projected indirectly on to the sensor contact surface 4 (surface) with the aid of masks and, in the process, by using the requisite number of light passes (laser beam passes) being introduced into the sensor contact surface 4 or respectively removed from the sensor contact surface 4, which will not be explained in more detail.

After that, a further step c) may be implemented, according to which the sensor workpiece 1 with the adhesive-laminated sensor contact surface 4 is arranged on a defined surface region of the body component surface 3. Finally, a step d) is implemented, according to which a mechanically acting contact pressure 8 is subsequently exerted on the two joint partners (sensor workpiece 1 and body component 2), with which the adhesive-laminated sensor contact surface 4 and the body component surface region 3 are pressed together.

This general illustration is expanded by the following measures. For example, it is proposed that, following step b) with a subsequent step f), the sensor workpiece 1 executed with the adhesive-laminated patterned sensor contact surface 4 be subjected in a drying cabinet to what is known as annealing, as a result of which the (homogeneous) adhesion between the transfer contact region and the adhesive-laminated sensor contact surface 4 (laminated to the latter) is maximized. The measure intended [expediently] with step f) will follow the implementation of step c). In addition, it is recommended that, before step c), coarse and/or fine cleaning of the body component surface region 3 is carried out, since an unclean (contaminated) body component contact surface 3 will certainly hardly benefit the nondetachable joining of the two joint partners, which is completed following the conclusion of the measure according to step d). In addition, in order to improve (maximize) the adhesion just mentioned between the transfer contact adhesive and the adhesive-laminated sensor contact surface 4 (laminated with the latter), it is proposed that, before step d), the galleries 6 are closed in an airtight manner on one side and those galleries 6 are connected on the other side to a vacuum device or vacuum pump, so that a vacuum is then generated within the galleries 6. Since provision is made for the step d) to be implemented with the aid of a clamping device (which clamps around the two joint partners), a contact pressure 8 which is produced by pressing the contact surfaces of the two joint partners by means of the clamping device will be increased, given simultaneous application of the clamping device and the vacuum device, as far as a defined vacuum (generated by the vacuum device), which should be maintained for at least ten minutes.

Further expedient exemplary embodiments and developments of these measures will be added to these aforementioned measures. For example, provision is made that, according to step a), the adhesive layer 5 is implemented with a defined and constant layer thickness, which is laminated onto the sensor contact surface 4. It will also be mentioned that the unrolling of the transfer contact adhesive from a transfer roll will be carried out before step a).

Only after that will the lamination of the adhesive layer 5 [according to step a)] be implemented with a manual laminating roll, for example, with which the adhesive layer 5 is rolled onto one side of the sensor workpiece 1 under slight pressure. Using this measure, the intention is for inclusions of air bubbles between the sensor contact service 4 and the transfer contact adhesive to be prevented. The laminating operation, which is implemented with the aid of said manual laminating roll, should [just—according to a step e)] be repeated with an electrically operated laminating device, in which the transfer contact adhesive is unrolled from the transfer roll with a defined roll speed to the electrically operated laminating device and then rolled on under a defined contact pressure 8. By this means, homogeneous adhesion between the transfer contact adhesive and the sensor contact surface 4 can be ensured.

It is also proposed that step b) is implemented using laser lithography. In this case, the geometric patterns of the galleries 6 are transferred to the adhesive-laminated sensor contact surface 4 directly by means of a controllable laser beam from a movable laser source, said patterns being introduced into the sensor workpiece 1 with a configuration which extends three-dimensionally (viewed geometrically). Otherwise, there is also the possibility for those patterns of the galleries 6 to be projected onto the adhesive-laminated sensor surface 4 indirectly with the aid of the laser with the interposition of masks, but this procedure will not be considered in more detail.

The gallery cross section of the individual gallery 6 (what is known as the vacuum or air gallery) will generally correspond to that of a body of rotation, which will terminate rectilinearly at the sensor contact surface 4 of the sensor workpiece 1. In this case, said gallery cross section could be implemented with a parabolic or square or rectangular form, the gallery cross section being cut out rectilinearly from the sensor contact surface 7 and the galleries 6 arranged beside one another being arranged in a laminar fashion. In this case, the laser beam (employed when the lithography method is used) which will penetrate through the transfer adhesive will cut out the galleries 6 lithographically from the sensor workpiece 1 with a removal depth t, which is influenced by the intensity of the laser beam, which is regulated by a laser source addressing the laser beam, and the speed of travel of the laser source. The laser source is moved three-dimensionally (that is to say in all three directions of the Cartesian coordinate system). In addition, in correlation with the controllable laser beam intensity, there is therefore also the option of laminating the transfer contact adhesive onto the sensor contact surface 4 with a freely selectable layer thickness by means of readjusting and/or bringing the laser source up to the adhesive application.

Furthermore, it is added that step d) is implemented with a clamping device, by means of whose external clamping of the two joint partners a defined contact pressure 8 is transferred to the contact surfaces of the joint partners, whose front surfaces are opposite one another, and on the adhesive layer 5 layered in between. In this case, the even contact with the sensor workpiece 1 over its contact surface 4 will be loaded uniformly.

In summary, a method for nondetachably joining a sensor workpiece 1 to a body component 2 may be specified, with which an application of vacuum sensors advantageously becomes available.

The method substantially comprises the following steps, according to which, first of all, a crosslinked transfer contact adhesive is laminated onto the sensor workpiece 1 (sensor material) (FIGS. 2a, 2b). After that, the galleries 6 (air and/or vacuum galleries) are introduced into the sensor material of the sensor workpiece 1 lying underneath with the aid of laser lithography through the adhesive layer 5 (FIG. 2c). The sensor (sensor workpiece 1) is bonded to the body component surface region 3 of a body component 2 or to the surface of an item under test with the assistance of a specific clamping method which makes it possible for the sensor workpiece 1, designated the sensor, to make flat contact on the body component 2 with a defined contact pressure 8 (FIG. 2d). The invention is (expediently) suitable for the permanent and reproducible use of the vacuum sensors for crack detection during mechanical tests on "coupon", "component" and "full scale" items under test and within the context of "Structural Health Monitoring" (SHM) in aircraft operation. The proposed procedure leads to vastly improved adhesive properties of the vacuum sensors and thus guarantees their fault-free and reproducible use.

Using the method proposed, the following causal relationships appear.

- The transfer process may permit the application of a crosslinked contact adhesive. Because of its crosslinking, the tendency of the contact adhesive to creep may be minimized.
- The constant layer thickness of the transfer contact adhesive may ensure homogeneous dynamic-mechanical properties of the adhesive layer between sensor and item under test surface.
- As a result of the adhesive thickness, which can be chosen variably as desired, the interaction between adhesive and joint part surface can be adjusted (optimally) in the sense of the dynamic-mechanical adhesion.
- On account of the subsequent laser lithography to the application of adhesive, there are less or essentially no adhesive residues in the vacuum and air galleries.
- The adhesive bonding of the sensors with a defined and reproducible contact pressure may ensure essentially homogeneous and good adhesion between the adhesive and the surface of the item under test.

The application of the vacuum sensors in this way may prevent the occurrence of leakages and blockages of the vacuum and air galleries in the application phase.

In summary, it is believed that improved adhesive properties of the vacuum sensors are achieved by the method. By means of the new procedure in the application of vacuum sensors to crack detection in joints, the intention is to "guarantee" that the sensors operate in a fault-free and reproducible manner and have a long lifetime.

In addition, a vacuum sensor application, whose implementation in accordance with the method previously explained is proposed, will now be considered in more detail.

A vacuum sensor application or a vacuum sensor for monitoring structural integrity, precisely for "Structural Health Monitoring" (as it is designated and known in specialist circles), will be presented, in which a sensor workpiece 1 is positioned on a body component surface region 3 of a body component 2. This sensor workpiece 1 is connected nondetachably, seamlessly or firmly to said body component 2 within a defined region of the body component surface. The sensor workpiece 1, which is shown in FIG. 2a, is composed of a sensor material which is suitable for the implementation of the sensor functions of a vacuum sensor.

The structure of said vacuum sensor application—with a view of FIG. 2d—accordingly (considered generally) comprises said aforementioned body component 2, on which a sensor workpiece 1 positioned within a defined region of the even body component surface region 3 (an even body component surface) is nondetachably joined to the body component 2. An adhesive layer 5 is laminated to the sensor workpiece 1 on an even sensor contact surface 4. This adhesive layer 5 is placed on the sensor contact surface 4 so as to be distributed homogeneously. Furthermore, in correlation with FIG. 2c, it can be gathered from FIG. 2d that the geometric patterns of a plurality of galleries 6 are introduced into the sensor workpiece 1 (are removed), being removed so as to coincide with the structures of the adhesive layer 5 introduced into the adhesive-laminated sensor workspace 1. These galleries 6 are arranged to lie beside one another in a laminar fashion. They are implemented by using known radiation methods, preferably with the aid of laser lithography, by using a light beam, preferably a laser beam.

The sensor workpiece 1, which is illustrated on its own in FIG. 1, is box-like or layer-like, a box shape or a cube shape (not illustrated separately) [as a special form of a box] being closer to reality.

The sensor contact surface 4 arranged underneath the sensor workpiece 1 will accordingly have a rectangular or square shape. According to the pattern of FIG. 2c, the sensor contact surface 4 of the sensor workpiece 1 is coated with the adhesive layer 5. The adhesive layer 5 is applied to the sensor contact surface 4 with a tool suitable for the purpose, the surface of the adhesive layer 5 which is able to adhere accordingly being square or rectangular and being layered virtually congruently with the sensor contact surface 4. Therefore, a layer structure is implemented in which the height of the sensor workpiece 1 or the distance between the bottom and top surface of the sensor workpiece 1 of the box-like or cube-like shape or the layer thickness a of a sensor workpiece 1 formed in the manner of a layer, for example, is greater than the layer thickness b of the adhesive layer 5.

Returning to the galleries 6 mentioned previously, it is additionally explained that the individual gallery 6 is implemented with a removal depth t which is limited by said body component surface region 3 of the body component 2 and is continued into the sensor workpiece 1.

For example, one embodiment of the galleries 6 which have a uniform appearance can be gathered from FIGS. 2c and 2d. This type of gallery 6 is removed vertically with respect to the top or bottom surface of the sensor workpiece 1, presented by way of example, of the shape of a box, whose gallery cross section corresponds to that of a parabola (open downward—toward the adhesive layer 5). The removal direction of those exemplary galleries 6 will take place in the direction of the abscissa of the parabola, those exemplary galleries 6 being removed with a removable depth t which (already) begins at the exposed surface of the adhesive layer 5 of the aforementioned layer structure that is capable of adhering and will end at the origin of the parabola on the abscissa within the sensor workpiece 1.

On the other hand, embodiments of galleries 6 having different types of geometric configuration and a different gallery cross section are conceivable, being machined into the sensor workpiece 1 and led through the adhesive layer 5. Here, appropriate galleries 6 are imagined whose geometric configuration (based on the pattern of an individual gallery 6) is machined into the sensor workpiece 1 with a gallery cross section which is not square or rectangular but comparable with a non-cylindrical longitudinal section. Galleries 6 of this type will have a physically variable gallery cross section which is machined into the sensor workpiece 1.

On the other hand, galleries 6 which have a uniform geometric configuration are machined into the sensor workpiece 1 with a uniform gallery cross section. One conceivable embodiment, which relates to the exemplary pattern according to FIGS. 2c and 2d, is given in the case of an implementation of the uniform gallery cross section with a parabolic cross-sectional shape, the opening of the parabola, passing through the sensor contact surface 4, terminating at the surface of the adhesive layer 5 of the aforementioned layer structure which is capable of adhering in accordance with the pattern of FIG. 2c.

Another exemplary embodiment of galleries 6 takes account of the fact that the uniform gallery cross section of an individual gallery 6 is implemented with a triangular cross-sectional shape, the opening of the triangle, which is arranged opposite the angle enclosed by the two sides of the triangle, ending with the sensor contact surface 4. In this case, the implementation of a triangular cross-sectional shape with the configuration of an equilateral triangle will be thought of.

In addition, a further embodiment of galleries 6 whose uniform gallery cross section is implemented with a trapezoidal cross-sectional shape will be taken appropriately into account; the opening of the trapezium, which is arranged opposite the top surface of the trapezium, should end with the sensor contact surface 4.

The arrangement of those galleries 6 which are let into the layer structure in a plurality and which as a rule will have a uniform gallery cross section will be taken into account in the overall product, that is to say the vacuum sensor application, with a gallery architecture according to which the course of the galleries introduced is implemented with the sides parallel to the longitudinal or broad side or extending transversely with respect to the congruently located layers of the layer structure, without any gallery crossing.

As a rule, as can be seen from FIGS. 2a to 2d, a gallery course parallel to the side or the longitudinal side or broad side is implemented, since a gallery course chosen to run transversely in this respect with respect to the congruently located layers of the layer structure, which is expediently implemented without any crossing of the galleries 6, will certainly rather form the exception.

With regard to the aforementioned adhesive layer 5, it is further added that this is generally implemented uniformly and preferably with a low layer thickness b in such a way that the layer thickness b of the adhesive layer 5 is implemented with a thin layer application.

Of course, the adhesive layer 5 can also be implemented with a thicker layer thickness b which is thicker than said thin layer thickness b; only then, possibly further special measures must be taken which will correlate with the capabilities of the adhesive used, for example its viscosity, its flow behavior, its temperature resistance, its resistance with respect to the nearer environment at the place of use, etc. and/or with further local precautions at the location at which the layer arrangement is put in place within said defined position region on the even body component surface of the body component 2, in order that no adhesive or other undesired deposits or other solid particles etc. penetrate into the gallery 6 (for reasons of cleanness or, respectively, ensuring said promised fault-free and reproducible mode of operation of the vacuum sensor application), as a result of which blockages or contamination of the open (free) gallery cross section will occur.

The adhesive layer 5 is generally implemented with a contact adhesive, preferably a transfer contact adhesive that can be laminated. The general statement: "contact adhesive" is chosen because other types of adhesive which adhere on contact and which are not considered in the following text can be entirely suitable for implementing the adhesive layer 5 on account of their characteristics and their technological handling but will not be discussed in more detail.

By way of example, as based on FIGS. 2b to 2d and 3 and 4, it is proposed that the adhesive layer 5 is implemented with a crosslinked transfer contact adhesive with little tendency to creep. This transfer adhesive should be made capable of implementing adhesion between the sensor workpiece 1 (the sensor contact surface 4 of the sensor workpiece 1) and the body component 2 (the body component surface region 3 of the body component 2). Using this, increased cohesion of the two joint partners (sensor workpiece 1 and body component 2) at the joints by means of a nondetachable joint is implemented.

The adhesive layer 5 may be implemented with a crosslinked transfer contact adhesive with little tendency to creep, which is capable of implementing sufficiently high adhesion for the firm and weathering-independent cohesion of the joint partners between the sensor workpiece 1 at the sensor contact surface 4 and the body component 2 at the body component surface region 3.

The transfer contact adhesive is capable of developing, at the contact surfaces of the sensor contact surface 4 and at the body component surface region 3, a dynamic-mechanical and homogeneous adhesion which is implemented with an adhesive force (in the peel test) of 20 to 50 N/25 mm.

The transfer contact adhesive is an adhesive which can be unrolled, can be unrolled from a transfer roll and is arranged (deposited) on the even surface of the sensor workpiece 1 or on the bottom box surface of the sensor workpiece 1, using aids suitable for the purpose. This adhesive is localized with a defined and constant layer thickness b which is suitable for being nondetachably joined to the body component surface region 3 of the body component 2, which is implemented under the influence of a defined and reproducible contact pressure acting on the two joint partners. An acrylate contact adhesive, which should have a layer thickness b of about 25 µm, is proposed for the use.

The aforementioned sensor material of the sensor workpiece 1 relates to a polymer material, whose use preferably with a polyimide is envisaged. With regard to the latter, the use of what is known as Kapton film is proposed, which is implemented with a film thickness of about 125 µm.

For the purpose of introducing (removing) all the aforementioned galleries 6 and more, which will be discussed later, use is made of a laser beam which, for example, is provided by a pulsed excimer beam. The excimer beam is aimed at the adhesive-laminated sensor workpiece 1 with a pulse energy of about 400 mJ.

With a glance at FIGS. 2c and 2d, in order to remove the galleries 6 of parabolic (uniform) gallery cross section, said excimer beam used is preferably placed vertically on the sensor contact surface 4. In this case, the excimer beam could also be placed at various angles of attack with respect to the sensor contact surface 4 if (if required) various types of galleries of, for example, different configurations (for whatever reasons) laminated uniformly are to be removed. An angle of attack is considered which is specified with an angular range from −45° to +45°, which the laser beam will form with the sensor contact surface.

The transfer adhesive of the adhesive layer 5 used has the capability, under the influence of the penetrating light beam, of cutting out the transfer contact adhesive with the passage cross section of the light beam at the point of passage of the light over the layer thickness b of the transfer adhesive as a result of residue-free adhesive evaporation without microscopic adhesive residue.

Mention is also made of the fact that the gallery depth corresponding to the removal depth t of those galleries 6 of uniform geometric configuration is implemented at about 100 μm, which is subsumed by the layer thickness b of the adhesive layer 5 and which is determined by the depth of the relevant gallery 6 removed within the sensor workpiece 1.

By way of example, the depth of the relevant gallery 6 removed within the sensor workpiece 1 should be implemented with 75 μm.

The use of the vacuum sensor application is seen, for example, predominantly on a body component 2 whose material relates to an appropriate metal (of a generally designated type) or a metal laminate. Added to this, uses on a composite material are realistic. Thought is also given to the fact that the surfaces of the metallic materials are coated with a layer of bonding primer or ink. This body component 2, specified as an item under test, counts as having to be monitored by means of suitable "Structural Health Monitoring", in order for example, as based on the different types of materials of the structure(s) of an aircraft, to detect the formation of cracks in good time on the aircraft structure and, respectively, to implement the finding of cracks in joints during aircraft operation taking place, and by means of those vacuum/air sensors which are embodied with those galleries (vacuum and air galleries).

It remains to mention the fact that the following embodiments of a vacuum sensor application which differ with regard to the design already presented should be of interest. The latter is in accordance with the two further proposed applications of the structure according to which these two embodiments of a vacuum sensor application for "Structural Health Monitoring" are likewise implemented with a body component 2 on which a sensor workpiece 1, to which an adhesive layer 5 is laminated on an even sensor contact surface 4 and is put in place so as to be distributed essentially homogeneously there, is positioned within a defined region of an even body component surface and is nondetachably joined to the body component 2.

Figure 3:
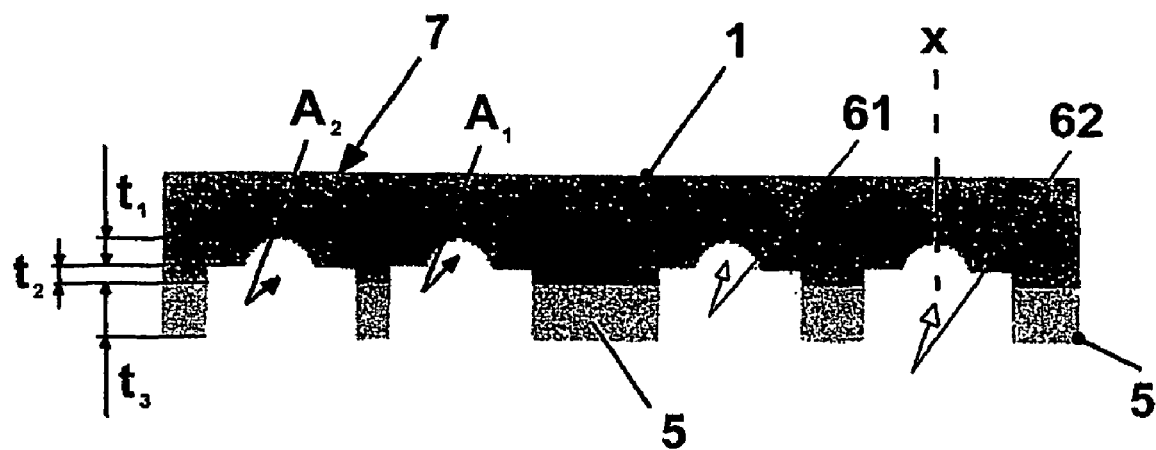
FIG. 3 shows the adhesive-laminated sensor workpiece according to FIG. 2b with the arrangement of various types of removed galleries according to an exemplary embodiment of the present invention.

The differences a for further vacuum sensor application consist in the fact that the geometric patterns of a plurality of first galleries 61 of uniform configuration, for example parabolic appearance, having a first gallery cross section A1 and a first removal depth t1, are arranged so as to lie beside one another in a laminar fashion according to FIG. 3, and the geometric patterns of a plurality of second galleries 62 of uniform configuration, for example rectangular appearance, having a second (for example rectangular) gallery cross section A2 and a second removal depth t2, which may correlate with the width of the rectangle, are introduced into the sensor workpiece 1.

The first and second galleries 61, 62 are in each case removed along a removal axis x which is perpendicular to a sensor workpiece surface 7. This application takes account of the fact that the first removal depth t1 is greater than the second removal depth t2. Added to this is the fact that the second gallery cross section A2 is implemented so as to be greater than the first gallery cross section A1, the geometric pattern of the individual second gallery 62 with the structure of the adhesive layer 5, introduced into the adhesive-laminated sensor workpiece 1, being removed along said removal axis x with a third removal depth t3, which corresponds to the thickness of the adhesive layer 5.

Figure 4:
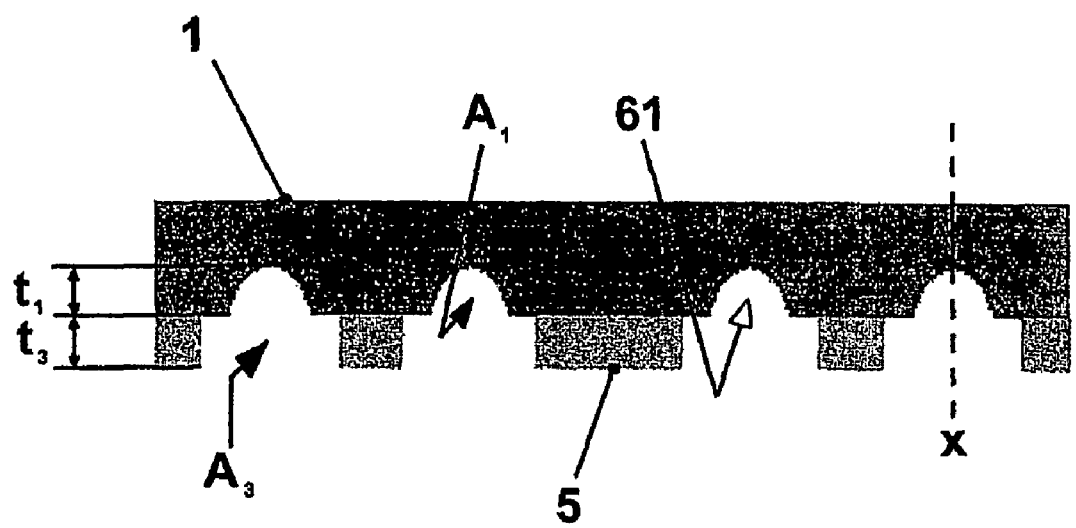
FIG. 4 shows the adhesive-laminated sensor workpiece according to FIG. 2b with the modified arrangement of various types of removed galleries according to an exemplary embodiment of the present invention.

It is believed that the differences for another vacuum sensor application consist in the fact that the geometric patterns of a plurality of first galleries 61 of uniform configuration are introduced into the sensor workpiece 1 with a first gallery cross section A1 and a first removal depth t1 which, according to FIG. 4, are arranged lying beside one another in a laminar fashion, the first galleries 61 in each case being removed along a removal axis x which is perpendicular to a sensor workpiece surface 7. The geometric pattern of the individual first gallery 61 is in each case removed in a stepped manner with the structure introduced into the adhesive-laminated sensor workpiece 1 along said removal axis x with a third removal depth t3, which corresponds to the thickness of the adhesive layer 5, and a third gallery cross section A3, the third removal depth t3 being less than or equal to or greater than the first removal depth t1 and also the third gallery cross section A3 being larger than the first gallery cross section A1.

With regard to the three exemplary embodiments presented for another vacuum sensor application, the following is added. As already indicated, the patterns of a plurality of galleries 6, 61, 62, what are known as the vacuum and/or air galleries, are transferred into the sensor material 1 in accordance with the patterns of FIG. 2c by using known radiation methods, for example with the aid of laser lithography, by removing adhesive layer 5 and sensor material. The material removal is carried out by the evaporation of adhesive and sensor material. The depth of the individual gallery is controlled by the number of repetitions of the laser radiation process. The removal rate of the galleries is influenced by the speed of travel, the intensity and the focusing of the laser beam. The width of the galleries is set by the number of repetitions of the laser beam process, in addition to the diameter of focus, with a simultaneous parallel offset of the laser beam track. With layer by layer removal and simultaneously optimized operating parameters (feed speed, diameter of focus, intensity), no macroscopic contaminants remain in the galleries.

In the case of higher compressive loading of the sensor implemented with the gallery, such as for example in the integral application for monitoring cracks between two riveted metal sheets belonging to a structure, it is recommended, depending on the viscosity of the adhesive used, to remove some of the adhesive on both sides of the galleries down to the sensor workpiece 1 in the manner described previously. As a result, the adhesive is offered additional space for volume expansion and the risk of a reduction in the cross section of the galleries is reduced. In addition, in this region worked free of adhesive, in a parallel arrangement to the air or vacuum galleries, additional galleries, which are specified with a second gallery 62 or said third gallery (having a third gallery cross section A3 and a third removal depth t3), what are known as protective galleries, are machined into the sensor workpiece 1 in the manner described above. In the event of higher compressive loading of the sensor implemented with the galleries, these protective galleries offer additional space for the volume expansion of the adhesive and, in this way, counteract the risk of a reduction in a cross section of the galleries by the adhesive.

Added to this is the fact that the alternative measures, which go back to those materials of the elements and their properties (adhesive, sensor and item under test material) proposed for the use and the laser used, which are proposed with regard to the (first) embodiment presented at the beginning for a vacuum sensor application according to FIGS. 2a to 2b, can also be transferred to those embodiments for a vacuum sensor application according to FIGS. 3 and 4, if they are compatible.

With regard to a possible implementation of said vacuum sensor application, at the start of the exemplary embodiments, the impression was given that all the generally specified steps a) to d), which were presented by using the example of said (first) embodiment presented at the start in accordance with FIGS. 2a to 2b, were comprehensible.

In addition, alternative refinements of these steps (specified generally) can be gathered from the above statements.

To the extent that this has not yet been done, it is added to the embodiments that there is also the possibility that the patterns and the galleries 6 are projected onto the sensor contact surface 4 (surface) indirectly with the aid of masks and, in the process, with the required number of light passes (laser beam passes), introduced into the sensor contact surface 4 or, respectively, removed from the sensor contact surface 4, although this will not be discussed in detail.

Following this, a further step c) is implemented, according to which the sensor workpiece 1 with the adhesive-laminated sensor contact surface 4 is arranged on a defined region of the area of the body component surface 3. Finally, a step d) is implemented, according to which a mechanically acting contact pressure 8 is subsequently exerted on both the joint partners (sensor workpiece 1 and body component 2), with which the adhesive-laminated sensor contact surface 4 and the body component surface region 3 are pressed together.

This general illustration may be expanded by the following measures according to further exemplary embodiments of the present invention. For example, it is proposed that the sensor workpiece 1 implemented with the adhesive-laminated patterned sensor contact surface 4 is subjected in a drying cabinet to what is known as annealing, as a result of which the (homogeneous) adhesion between the transfer contact adhesive and the adhesive-laminated sensor contact surface 4 (laminated to the latter) is maximized. A coarse and/or fine cleaning of the body components of this region 3 may be carried out, since an unclean (contaminated) body component contact surface 3 would certainly hardly benefit the nondetachable joining of the two joint partners. In addition, in order to improve (maximize) the adhesion just mentioned between the transfer contact adhesive and the adhesive-laminated sensor contact surface 4 (laminated to the latter) it is proposed that the galleries 6, if appropriate, are closed in an airtight manner on one side and those galleries 6 are connected on the other side to a vacuum device, for example a vacuum pump, so that a vacuum is then generated within the galleries 6.

Since provision is made for the compression of the two joint partners to be implemented with the aid of a clamping device (clamping around the two joints partners), a contact pressure 8, which is produced by pressing on the contact surfaces of the two joint partners by means of the clamping device, is increased, given simultaneous application of the clamping device and the vacuum device, as far as a defined vacuum (generated by the vacuum device), which should be maintained for at least ten minutes.

Mention is also made of the fact that the transfer contact adhesive is unwound from a transfer roll. Only after the transfer contact adhesive has been unrolled is the lamination of the adhesive layer 5 implemented, for example with a manual laminating roll, with which the adhesive layer 5 is rolled onto one side of the sensor workpiece 1 under slight pressure. Using this measure, the intention is for inclusions of air bubbles between the sensor contact service 4 and the transfer contact adhesive to be prevented.

The laminating operation, which is implemented with the aid of said manual laminating roll, should be repeated with an electrically operated laminating device, in which the transfer contact adhesive is unrolled from the transfer roll with a defined roll speed to the electrically operated laminating device and then rolled on under a defined contact pressure 8. By this means, homogeneous adhesion between the transfer contact adhesive and the sensor contact surface 4 can be ensured.

The geometric patterns of the galleries 6 are transferred directly to the sensor contact surface 4 from a movable laser source by means of a controllable laser beam (excimer beam) which (viewed geometrically) is introduced into the sensor workpiece 1 with a configuration extending three-dimensionally. Otherwise, there is also the possibility that the pattern of the galleries 6 is projected onto the sensor workpiece surface 4 with the aid of the laser indirectly with the interposition of masks, but this procedure will not be considered in more detail.

The gallery cross section of the individual gallery 6 (what is known as the vacuum or air gallery) generally corresponds to that of a body of rotation which will terminate rectilinearly at the sensor contact surface 4 of the sensor workpiece 1. In this case, said gallery cross section could theoretically be implemented with any desired form, a non-square or non-rectangular or a parabolic or trapezoidal or else a square or rectangular form preferably being preferred, and the gallery cross section being cut out so as to run rectilinearly (vertically) or with a suitable angle of attack of the sensor contact surface 7. In this case, the laser beam (employed when the lithography process is used) will cut the galleries 6 out of the sensor workpiece 1 lithographically with a removal depth t which is influenced by the intensity of the laser beam, which is controlled by a laser source that addresses the laser beam, and the speed of travel of the laser source. The laser source is moved three-dimensionally (that is to say in all three directions of the Cartesian coordinate system). In addition, in correlation with the controllable laser beam intensity, there is therefore also the option of laminating the transfer contact adhesive onto the sensor contact surface 4 with a freely selectable layer thickness by means of readjusting and/or bringing the laser source up to the adhesive application.

It is further added that the action of pressing the two joint partners together is implemented with a clamping device, by means of whose external clamping of the two joint partners a defined contact pressure 8 is transferred to the contact surfaces of the joint partners, whose front surfaces are opposite one another, and to the adhesive layer 5 layered in between. In this case, the even contact with the sensor workpiece 1 over its contact surface 4 is loaded uniformly.

The invention relates to a vacuum sensor application for the implementation of "Structural Health Monitoring" (SHM) and a method for nondetachably joining a sensor workpiece to a body component according to the preamble of claims 1, 15, 46 and 47. A vacuum sensor application and a method for its implementation are specified with which "Structural Health Monitoring" (SHM) on structures is implemented, in order to monitor the action of finding cracks in joints, for example in aircraft operation, said application being able to be implemented in an efficient manner without additional effort on reworking.

The vacuum sensor application for Structural Health Monitoring has a body component, on which a sensor workpiece, to which an adhesive layer is laminated onto an even sensor contact surface and is placed thereon so as to be distributed homogeneously, is positioned within a defined region of an even body component surface and is nondetachably joined to the body component. The geometric patterns of a plurality of galleries, which are arranged lying beside one another in a laminar fashion, are introduced into the sensor workpiece, and are removed congruently with the structures of the adhesive layer introduced into the adhesive-laminated sensor workpiece.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

List of Reference Signs

1 Sensor workpiece
2 Body component
3 Body component surface region
4 Sensor contact surface
5 Adhesive layer; transfer adhesive
6 Gallery/ies
61 First gallery
62 Second gallery
7 Sensor workpiece surface
8 Contact pressure
a Layer thickness
b Layer thickness
A1 First gallery cross section
A2 Second gallery cross section
t Removal depth
t1 First removal depth
t2 Second removal depth
t3 Third removal depth

The invention claimed is:

1. A method of firmly joining a sensor workpiece to a body component, in which the sensor workpiece which comprises a sensor material, is positioned on a body component surface region of the body component and is firmly joined to the body component, said method comprises the steps of:
   a) firstly, laminating an adhesive layer which is provided by a cross-linked transfer contact adhesive to a sensor contact surface of the sensor workpiece;
   b) then, by using known radiation methods, transferring geometric patterns of a plurality of galleries to be arranged in a laminar fashion to the sensor contact surface by a light beam that penetrates the transfer contact adhesive, which are subsequently introduced into the sensor workpiece and, in the process, are removed congruently with the structures of the adhesive layer introduced into the sensor workpiece;
   c) subsequently arranging the adhesive-laminated patterned sensor contact surface on a defined surface region of the body component surface; and
   d) subsequently exerting a mechanical pressure on the two joint partners, by which the adhesive-laminated patterned sensor contact surface and the body component surface region are pressed together.

2. The method as claimed in claim 1, wherein, according to step a), the adhesive layer is implemented with a defined constant layer thickness, which is laminated onto the sensor contact surface.

3. The method as claimed in claim 1, wherein step a) is preceded by a step of unrolling the transfer contact adhesive from a transfer roll, which is supplied to a manual laminating roll, and during the step of laminating the adhesive layer, said manual laminating roll is used to roll the adhesive layer onto the sensor contact surface of the sensor workpiece under slight contact pressure in such a way that air bubble inclusions between the sensor contact surface and the transfer contact adhesive are prevented.

4. The method as claimed in claim 3, wherein with a step e) the laminating operation is repeated with an electrically operated laminating device, in which the transfer contact adhesive is unrolled from the transfer film with a defined rolling speed to the electrically operated laminating device and is then rolled on under a defined contact pressure in such a way that a substantially homogeneous adhesion between the transfer contact adhesive and the sensor contact surface is achieved.

5. The method as claimed in claim 4, wherein with a subsequent step f), the sensor workpiece with the adhesive-laminated patterned sensor contact surface is then subjected to annealing in a drying cabinet, by which means the adhesion is maximized.

6. The method as claimed in claim 1, wherein step b) is implemented by using laser lithography in such a way that the geometric patterns of the plurality of galleries are transferred to the adhesive-laminated sensor contact surface directly from a movable laser source by means of a controllable laser beam and are introduced three-dimensionally into the sensor workpiece, or are projected onto the adhesive-laminated sensor contact surface indirectly, with the interposition of masks.

7. The method as claimed in claim 6, wherein a geometric pattern of the galleries, is transferred.

8. The method as claimed in claim 7, wherein a cross section of a respective gallery of the plurality of galleries generally corresponds to that of a body of rotation which ends rectilinearly at the sensor contact surface, which is preferably implemented with a parabolic form whose parabola opens toward the sensor contact surface, or a square or rectangular form, the gallery cross section being cut out from the sensor contact surface so as to extend rectilinearly; wherein the plurality of galleries consists of at least one of a vacuum gallery and an air gallery.

9. The method as claimed in claim 6, wherein a removal depth of the laser beam passing through the transfer contact adhesive and penetrating into the sensor workpiece is varied on the basis of its intensity and a speed of travel of the laser source.

10. The method as claimed in claim 6, wherein the laser source is displaced three-dimensionally and the transfer contact adhesive is laminated to the sensor contact surface with a freely selectable layer thickness by means of tracking the laser source to the adhesive application, bringing the laser source up to the adhesive application or both thereof.

11. The method as claimed in claim 1, wherein before step c) coarse cleaning, fine cleaning or both thereof are carried out on the body component surface.

12. The method as claimed in claim 1, wherein step d) is implemented with a clamping device by means of whose external clamping of the two joint partners, a defined contact pressure is transferred to the contact surfaces of each of the two joint partners, whose front faces are opposite one another, and to the adhesive layer layered in between, in such a way that an even contact of the sensor workpiece is loaded uniformly over the sensor contact surface of the sensor workpiece.

13. The method as claimed in claim 1, wherein before step d) the plurality of galleries are closed in an airtight manner on one side and, on the other side, are connected to a vacuum device and a vacuum is then generated within the plurality of galleries.

14. The method as claimed in claim 13, wherein, by using the clamping device and the vacuum device, the contact pressure is increased up to a defined vacuum, which is maintained for at least ten minutes.

15. A vacuum sensor for Structural Health Monitoring, comprising a body component, at which a sensor workpiece is positioned within a defined region of an even surface region of the body component and is firmly joined to the body component, said sensor workpiece is provided with an adhesive layer laminated onto an even contact surface of the sensor workpiece and said adhesive layer is arranged on the contact surface so as to be distributed substantially homogeneously, wherein geometric patterns of a plurality of galleries, which are arranged lying beside one another in a laminar fashion, are introduced into the sensor workpiece and are removed congruently with a plurality of structures of the adhesive layer introduced into the adhesive-laminated sensor workpiece.

16. The vacuum sensor as claimed in claim 15, wherein a respective gallery of the plurality of galleries is implemented with a removal depth which is limited by a body component surface region of the body component and is continued into the sensor workpiece.

17. The vacuum sensor as claimed in claim 15, wherein the plurality of galleries are machined into the sensor workstation with a different type of geometric configuration and a different gallery cross section.

18. The vacuum sensor as claimed in claim 15, wherein the plurality of galleries are machined into the sensor workpiece with a substantially uniform geometric configuration and with a substantially uniform gallery cross section.

19. The vacuum sensor as claimed in claim 18, wherein the substantially uniform gallery cross section is implemented with a parabolic cross-sectional form, an opening of the parabola ending with the contact surface of the sensor workpiece.

20. The vacuum sensor as claimed in claim 18, wherein the substantially uniform gallery cross section is implemented with a triangular cross-sectional form, an opening of the triangle, which is arranged opposite an angle formed by two sides of the triangle, ending with the sensor contact surface of the sensor workpiece.

21. The vacuum sensor as claimed in claim 20, wherein the triangular cross-central form is implemented with a configuration of an equilateral triangle.

22. The vacuum sensor as claimed in claim 15, wherein the substantially uniform gallery cross section is implemented with a trapezoidal cross-sectional form, an opening of the trapezium, which is arranged opposite the top surface of the trapezium, ending with the contact surface of the sensor workpiece.

23. The vacuum sensor as claimed in claim 17, wherein a geometric configuration of a respective gallery of the plurality of galleries is machined into the sensor workpiece with a non-square or non-rectangular gallery cross section which is comparable with a non-cylindrical longitudinal section.

24. The vacuum sensor as claimed in claim 23, wherein a three-dimensionally variable gallery cross section is machined into the sensor workpiece.

25. The vacuum sensor as claimed in claim 15, wherein the plurality of galleries which are removed congruently from the sensor workpiece and the adhesive layer are implemented by using known radiation methods, preferably with the aid of laser lithography, by using a light beam, preferably a laser beam.

26. The vacuum sensor as claimed in claim 15, wherein, by using the sensor workpiece, which is box-like or layer-like and whose sensor contact surface is square or rectangular, and the adhesive layer, whose adhesive surface is square or rectangular and is layered substantially congruently with the contact surface of the sensor workpiece, a layer structure is implemented in which a first layer thickness of the sensor workpiece is greater than a second layer thickness of the adhesive layer.

27. The vacuum sensor as claimed in claim 26, wherein account is taken of an arrangement of the plurality of galleries with a gallery architecture according to which a course of a respective gallery of the plurality of galleries is implemented substantially parallel with the sides or the longitudinal or broad side or extending transversely with respect to the congruently located layers of the layer structure, without gallery crossing.

28. The vacuum sensor as claimed in claim 26, wherein the adhesive layer is implemented substantially uniformly and with a low layer thickness.

29. The vacuum sensor as claimed in claim 28, wherein the second layer thickness of the adhesive layer is implemented with a thin layer application.

30. The vacuum sensor as claimed in claim 28, wherein the adhesive layer is implemented with a transfer contact adhesive that can be laminated.

31. The vacuum sensor as claimed in claim 30, wherein the adhesive layer is implemented with a cross-linked transfer contact adhesive with a low tendency to creep, which is capable of implementing adhesion between the contact surface of the sensor workpiece and the body component surface region of the body component.

32. The vacuum sensor as claimed in claim 30, wherein the transfer contact adhesive is adapted for developing, on the contact surfaces of the sensor contact surface and of the body component surface region, a dynamic-mechanical and homogeneous adhesion which is implemented with an adhesive force of 20-50 N/25 mm.

33. The vacuum sensor as claimed in claim 30, wherein the transfer contact adhesive is an adhesive which can be unrolled from a transfer roll with a defined and constant second layer thickness and is suitable for being nondetachably joined to the body component surface region of the body component, which is implemented under the influence of a defined and reproducible contact pressure acting on the two joint partners.

34. The vacuum sensor as claimed in claim 30, wherein the contact adhesive is preferably an acrylate contact adhesive, which is used with a second layer thickness of about 25 µm.

35. The vacuum sensor as claimed in claim 31, wherein the sensor material of the sensor workpiece is a polymer material.

36. The vacuum sensor as claimed in claim 35, wherein the polymer material is preferably implemented with a polyimide.

37. The vacuum sensor as claimed in claim 36, wherein the polyimide is a Kapton film, which is implemented with a film thickness of about 125 µm.

38. The vacuum sensor as claimed in claim 25, wherein the laser beam used is a pulsed excimer laser beam, which is aimed at the adhesive-laminated sensor workpiece with a pulse energy of 400 mJ.

39. The vacuum sensor as claimed in claim 38, wherein the laser beam is set on the sensor contact surface at various angles of attack, preferably vertically on the sensor contact surface.

40. The vacuum sensor as claimed in claim 39, wherein the angle of attack is based on an angular range from −45° to +45° which the laser beam forms with the contact surface.

41. The vacuum sensor as claimed in claim 30, wherein the transfer adhesive of the adhesive layer has the capability under the influence of the penetrating light beam, of cutting out the transfer contact adhesive with the passage cross section of the light beam at the point of passage of the light over the second layer thickness of the transfer adhesive as a result of residue-free adhesive evaporation without microscopic adhesive residue.

42. The vacuum sensor as claimed in claim 18, wherein the gallery depth of those galleries of substantially uniform geometric configuration, correlating with the removal depth, is implemented with about 100 μm, which is subsumed by the layer thickness of the adhesive layer and which is determined within the depth of the relevant gallery removed from the sensor workpiece.

43. The vacuum sensor as claimed in claim 42, wherein the depth of the relevant gallery removed within the sensor workpiece is implemented with 75 μm.

44. The vacuum sensor as claimed in claim 15, wherein a material of the body component is an appropriate metal, a metal laminate or a composite material.

45. The vacuum sensor as claimed in claim 44, wherein surfaces of the sensor workpiece are coated with a layer of bonding primer or ink.

46. The vacuum sensor of claim 15, wherein the vacuum sensor is a vacuum sensor application.

47. A vacuum sensor application for Structural Health Monitoring, comprising a body component, on which a sensor workpiece, to which an adhesive layer is laminated onto an even sensor contact surface and is placed thereon so as to be distributed homogeneously, is positioned within a defined region of an even body component surface and is nondetachably joined to the body component, wherein geometric patterns of a plurality of first galleries of substantially uniform configuration with a first gallery cross section and a first removal depth, which are arranged lying beside one another in a laminar fashion, and the geometric patterns of a plurality of second galleries of uniform configuration with a second gallery cross section and a second removal depth are introduced into the sensor workpiece, the first and second galleries in each case being removed along a removal axis which extends from a sensor workpiece surface, and the first removal depth being greater than the second removal depth and the second gallery cross section being greater than the first gallery cross section, and the geometric pattern of the individual second gallery, in each case with the structure of the adhesive layer introduced into the adhesive-laminated sensor workpiece, being removed along said removal axis with a third removal depth which corresponds to a thickness of the adhesive layer.

48. A vacuum sensor application for Structural Health Monitoring, comprising a body component, on which a sensor workpiece, to which an adhesive layer is laminated onto an even sensor contact surface and is placed thereon so as to be distributed homogeneously, is positioned within a defined region of an even body component surface and is nondetachably joined to the body component, wherein a plurality of first galleries of uniform configuration with a first gallery cross section and a first removal depth, which are arranged lying beside one another in a laminar fashion, have geometric patterns which are introduced into the sensor workpiece, the first galleries in each case being removed along a removal axis extending from a sensor workpiece surface, and the geometric pattern of the individual first gallery, in each case with the structure introduced into the adhesive-laminated sensor workpiece, being removed in a stepped manner along said removal axis with a third removal depth, which corresponds to a thickness of the adhesive layer, and a third gallery cross section, the third removal depth being less than or equal to or greater than the first removal depth, and the third gallery cross section being greater than the first gallery cross section.

* * * * *